United States Patent [19]

Hart et al.

[11] Patent Number: 5,276,045
[45] Date of Patent: Jan. 4, 1994

[54] THIOFORMAMIDE DERIVATIVE, PROCESS FOR ITS PREPARATION, PHARMACEUTICAL COMPOSITION THEREOF AND TREATMENT METHOD

[75] Inventors: Terance W. Hart, Brentwood; Bernard Y. J. Vacher, Dageham; Roger J. A. Walsh, Rayleigh, all of England

[73] Assignee: Rhone-Poulenc Sante, France

[21] Appl. No.: 860,599

[22] Filed: Mar. 30, 1992

Related U.S. Application Data

[63] Continuation of Ser. No. 538,714, Jun. 15, 1990, abandoned.

[30] Foreign Application Priority Data

Jun. 16, 1989 [GB] United Kingdom ............ 8913863
Jun. 16, 1989 [GB] United Kingdom ............ 8913864

[51] Int. Cl.$^5$ .......... C07D 213/44; C07D 211/70; A61K 31/44
[52] U.S. Cl. ................ 514/357; 514/332; 514/340; 514/355; 546/262; 546/284; 546/330; 546/331
[58] Field of Search ........... 546/114, 138, 139, 234, 546/262, 284, 331; 514/256, 265, 307, 301, 311, 332, 357

[56] References Cited

U.S. PATENT DOCUMENTS

| | | | |
|---|---|---|---|
| 4,252,803 | 2/1981 | Webb | 514/415 |
| 4,959,385 | 9/1990 | Cook et al. | 514/431 |
| 5,064,843 | 11/1991 | Hart et al. | 514/346 |

FOREIGN PATENT DOCUMENTS 321274 6/1989 European Pat. Off. .
390693 10/1990 European Pat. Off. .
403398 12/1990 European Pat. Off. .

Primary Examiner—Mukund J. Shah
Assistant Examiner—Matthew V. Grumbling
Attorney, Agent, or Firm—Morgan & Finnegan

[57] ABSTRACT

A thioformamide derivative of the formula:

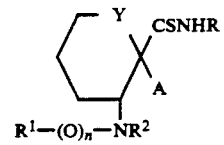

wherein R represents alkyl, A represents optionally substituted pyrid-3-yl, isoquinolin-4-yl, tetrahydroquinolin-3-yl, quinolin-3-yl, pyridazin-4-yl, pyrimid-5-yl, thiazol-5-yl, thieno[2,3-b]pyridin-5-yl, pyrazin-2-yl, indol-3-yl and thieno[3,2-b]pyridin-6-yl, or phenyl and Y represents a valency bond, methylene or ethylene, $R^2$ represents hydrogen, optionally substituted alkyl, cycloalkyl, cycloalkylalkyl, aryl, aralkyl, aryloxyalkyl, aromatic heterocyclylalkyl or aromatic heterocyclyloxyalkyl group or a group ZC(=O)— in which Z represents optionally substituted alkyl, aryl, or aromatic heterocyclic, n represents 0 or 1, and when n represents 0, $R^1$ may represent a hydrogen atom, optionally substituted alkyl, cycloalkyl, cycloalkylalkyl, aryl, aralkyl, aryloxyalkyl, aromatic heterocyclylalkyl or aromatic heterocyclyloxyalkyl group or a group ZC(=O)— or $ZSO_2$—, and when n represents 1, $R^1$ represents optionally substituted alkyl, benzyl, phenethyl, 1-naphthylmethyl, 2-naphthylmethyl or pyrid-3-ylmethyl radical and pharmaceutically acceptable salts thereof possess pharmacological properties.

11 Claims, No Drawings

THIOFORMAMIDE DERIVATIVE, PROCESS FOR ITS PREPARATION, PHARMACEUTICAL COMPOSITION THEREOF AND TREATMENT METHOD

This is a continuation of co-pending application Ser. No. 07/538,714, filed on Jun. 15, 1990, now abandoned.

FIELD OF THE INVENTION

This invention relates to new therapeutically useful thioformamide derivatives, to processes for their preparation and to pharmaceutical compositions containing them.

DETAILED DESCRIPTION OF THE INVENTION

The new thioformamide derivatives of the present invention are those compounds of the general formula (I) hereinafter depicted, wherein R represents a straight- or branched-chain alkyl radical containing from 1 to 14 carbon atoms, A represents an aromatic heterocyclic radical containing one or two nitrogen atoms (optionally substituted by a straight- or branched-chain alkyl or alkoxy radical containing 1 to 4 carbon atoms or by a halogen atom), selected from pyrid-3-yl, isoquinolin-4-yl, tetrahydroquinolin-3-yl, quinolin-3-yl, pyridazin-4-yl, pyrimid-5-yl, thiazol-5-yl, thieno[2,3-b]pyridin-5-yl, pyrazin-2-yl, indol-3-yl and thieno[3,2-b]pyridin-6-yl, or represents an optionally substituted phenyl group and Y represents a valency bond or an ethylene or preferably methylene radical, $R^2$ represents a hydrogen atom, an optionally substituted (as Z below) alkyl, cycloalkyl, cycloalkylalkyl, aryl, aralkyl, aryloxyalkyl, aromatic heterocyclylalkyl or aromatic heterocyclyloxyalkyl group or a group $ZC(=O)-$ in which Z represents an optionally substituted alkyl, aryl, e.g. phenyl, or aromatic heterocyclic, e.g. pyrid-3-yl, group, n represents 0 or 1, and when n represents 0, $R^1$ may represent a hydrogen atom, an optionally substituted (as Z) alkyl, cycloalkyl, cycloalkylalkyl, aryl, aralkyl, aryloxyalkyl, aromatic heterocyclylalkyl or aromatic heterocyclyloxyalkyl group or a group $ZC(=O)-$ or $ZSO_2-$, and when n represents 1, $R^1$ represents a straight- or branched-chain alkyl radical containing from 1 to 4 carbon atoms which is unsubstituted or substituted by one or more substituents selected from $C_{2-4}$-alkenyl, carboxy, $C_{2-5}$-alkoxycarbonyl, hydroxy, $C_{1-4}$-alkoxy, carbamoyl (unsubstituted or substituted by one or two $C_{1-4}$-alkyl groups), amino, $C_{1-4}$-alkylamino and di-$C_{1-4}$-alkylamino groups (e.g. $R^1$ may represent a methyl, 2-hydroxy-3-isopropyl-aminopropyl or 2-hydroxy-3-t.butylaminopropyl radical), or represents a benzyl, phenethyl, 1-naphthylmethyl, 2-naphthylmethyl or pyrid-3-ylmethyl radical each of which may be substituted on the ring by one or more halogen atoms or hydroxy, $C_{1-4}$-alkyl, $C_{1-4}$-alkoxy (alkoxy being unsubstituted or substituted as defined for alkyl groups represented by $R^1$), cyano, nitro, trifluoromethyl, carboxy, $C_{1-4}$-alkylamino, $C_{2-5}$-alkanoylamino or $C_{2-5}$-alkoxycarbonyl groups, and pharmaceutically acceptable salts thereof.

Preferably A represents 3-pyridyl, 6-chloropyrid-3-yl, 5-bromopyrid-3-yl, 3-quinolye, 4-isoquinolinyl or 5-pyrimidyl, or phenyl substituted in the 3 and/or 5 position with an electron-withdrawing group for example a cyano, nitro, trifluoromethyl, carbamoyl, carboxy, $C_{2-5}$-alkanoyl, $C_{2-5}$-alkoxycarbonyl or $C_{1-4}$-alkylsulphonyl group or a fluorine, chlorine or bromine atom, and optionally further substituted with halogen atom(s), $C_{1-4}$-alkyl or $C_{6-12}$-aryl (e.g. phenyl) group(s), or the phenyl group A may be substituted with halogen atom(s), $C_{1-4}$-alkyl or $C_{6-12}$-aryl (e.g. phenyl) group(s), or with substituents which together form a fused ring, for example a 2-naphthyl group.

The group A may represent, for example, the phenyl, 4-chlorophenyl, 3-trifluoromethylphenyl, 3-nitrophenyl, 3,4-dichlorophenyl or 2-naphthyl group.

Preferably Z represents a phenyl, pyrid-3-yl or thien-2-yl group or a straight- or branched-chain alkyl group (containing from 1 to 6 carbon atoms), each of which may be optionally substituted by one or more substituents selected from halogen atoms or hydroxy, $C_{1-4}$-alkyl, $C_{2-4}$-alkenyl, $C_{1-4}$-alkoxy, tetrahydropyranyloxy, cyano, nitro, trifluoromethyl, carboxy, benzoylamino, quaternary ammonium, amino, $C_{1-4}$-alkylamino and di-$C_{1-4}$-alkylamino groups (optionally substituted by hydroxy groups), $C_{2-5}$-alkoxy carbonylamino, $C_{2-5}$-alkanoylamino or $C_{2-5}$-alkoxycarbonyl groups or carbamoyl (unsubstituted or substituted by one or two $C_{1-4}$-alkyl groups in turn optionally substituted by hydroxy groups) two substituents on the nitrogen atom may together form a straight or branched chain divalent radical containing from 4 to 6 atoms in the chain which may contain a further heteroatom e.g. piperidinocarbonyl), or Z represents a benzyl, phenethyl, 1-naphthylmethyl, 2-naphthylmethyl or pyrid-3-ylmethyl radical.

The group Z may represent, for example, the phenyl, 4-fluorophenyl, 3,4-difluorophenyl, 4-methoxyphenyl, 2-carboxyphenyl, pyrid-3-yl, thien-2-yl, methyl, butyl, 2-carboxethyl, 2-methoxycarbonylethyl, hydroxymethyl, tetrahydropyranyloxymethyl, aminomethyl, t-butoxycarbonylaminomethyl, benzylaminomethyl, benzyl, phenethyl or N-methylpiperidinocarbonylethyl group.

Preferably $R^2$ represents the hydrogen atom. Amino groups $R^1R^2N-$ that may be mentioned are 1-phenylethylamino, 1-(1-naphthyl)ethylamino, 1-cyclohexylethylamino or 1-(pyrid-3-yl)ethylamino.

The presence of an amino group on the ring creates an asymmetry in the molecule which, in association with the adjacent asymmetric carbon atom, leads to 4 stereoisomers which, optionally, can be separated into 2 racemic pairs. The racemic pair and its enantiomers of the general formula (II) in which R, A and Y are as hereinbefore defined, i.e. the compounds in which the amino group is in the trans position relative to the group -CSNHR, are preferred.

Furthermore, in certain cases the substituents R, $R^1$ and $R^2$ contribute to stereoisomerism. All such forms are embraced by the present invention.

Especially important compounds of the present invention include those wherein at least one of the symbols has a value selected from the following:
(i) R represents methyl;
(ii) A represents 3-pyridyl;
(iii) Y represents methylene;
(iv) Z represents lower alkyl, e.g. methyl, or optionally substituted phenyl;
(v) $R^2$ represents hydrogen; and
(vi) $R^1$ represents hydrogen, lower alkyl, e.g. methyl or ethyl, optionally carrying a substituent selected from aryl, preferably naphthyl or optionally substituted phenyl (the said optional substituents on phenyl being preferably one or more halogen, preferably fluorine, atoms), or 3-pyridyl, cycloalkyl, e.g. cyclohexyl, and hydroxy groups, or represents a lower alkanoyl, preferably acetyl, or aroyl, preferably benzoyl, or arylsulphonyl, preferably phenylsulphonyl, group;

the other symbols being as hereinbefore defined, and their pharmaceutically acceptable salts.

Particularly important compounds of the present invention include the following:

AA. (±)-trans-2-benzyloxyamino-N-methyl-1-(3-pyridyl)cyclohexanecarbothioamide

AB. (±)-trans-2-methoxyamino-N-methyl-1-(3-pyridyl)cyclohexanecarbothioamide

AC. (±)-trans-2-(4-fluorobenzyloxyamino)-N-methyl-1-(3-pyridyl)cyclohexanecarbothioamide AD. (1S,2R)-2-(2,3,4,5, 6-pentafluorobenzyloxyamino)-N-methyl-1-(3-pyridyl)cyclohexanecarbothioamide AE. (±)-trans-2-(2-hydroxyethoxyamino-N-methyl-1-(3-pyridyl)cyclohexanecarbothioamide BA. (±)-trans-2-amino-N-methyl-1-(3-pyridyl)cyclohexanecarbothioamide BB. (±)-trans-2-benzamido-N-methyl-1-(3-pyridyl)cyclohexanecarbothioamide BC. (±)-trans-2-acetamido-N-methyl-1-(3-pyridyl)cyclohexanecarbothioamide BD. (2R,1S)-2-[(R)-1-phenylethylamino]-1-(3-pyridyl)cyclohexane-N-methylcarbothioamide BE. (2R,1S)-2-[(R)-1-(1-naphthyl)ethylamino]-1-(3-pyridyl) cyclohexane-N-methylcarbothioamide BF. (2R,1S)-2-[(R)-1-cyclohexylethylamino]-1-(3-pyridyl) cyclohexane-N-methylcarbothioamide BG. (±)-(2R,1S)-2-[(R)-1-(4-fluorophenyl)-ethylamino]-1-(3-pyridyl)cyclohexane-N-methylcarbothioamide CA. (±)-trans-N-methyl-2-phenylsulphonamido-1-(3-pyridyl)cyclohexanecarbothioamide CB. (±)-trans-N-methyl-2-phenylamino-1-(3-pyridyl)-cyclohexanecarbothioamide CC. (±)-trans-N-methyl-1-benzylamino-2-(3-pyridyl)-cyclohexanecarbothioamide CD. (−)-(1R,2S)-N-methyl-2-(3-pyridyl)methylamino-1-(3-pyridyl)-cyclohexanecarbothioamide The letters AA to CD are allocated to the compounds for easy reference later in the specification, e.g. in the Table and in the Examples.

The compounds have valuable pharmacological properties, in particular properties which are indicative of utility in the treatment and/or propylaxis of disorders associated with:

(1) vascular smooth muscle contraction including hypertension and other cardiovascular disorders such as congestive heart failure, and conditions associated with tissue ischemia such as angina, peripheral vascular disease and cerebrovascular disease;

(2) respiratory smooth muscle contraction including reversible airways obstruction and asthma;

(3) contraction of smooth muscle of gastro-intestinal tract, urinary bladder and uterus, including peptic ulcers, irritable bowel syndrome and diverticular disease; irritable bladder syndrome; and premature labor.

The compounds also have utility in the inhibition of head hair loss associated with male pattern baldness, by topical application.

For example, compounds of general formula (I) were submitted to:

Vaso-relaxant Activity Tests

The test methods used were adapted from those described by Winslow et al [Eur. J. Pharmacol., 131, 219–228 (1986)] and Karaki [J. Pharmacol. Methods, 18, 1–21 (1987)] for differentiating vaso-relaxant activity.

Test A: Activity against contractions induced by low K+ concentrations in the isolated rat aorta Thoracic aorta was removed from rats and transverse strips, denuded of endothelium, were suspended in a bath containing Krebs solution. The tension was recorded and a contraction induced by addition of 20 mM K+ (potassium ion) to the bathing solution. The test compound was added to the bath as a solution in increasing cumulative concentration. The concentration in the bathing solution of the test compound which reduced the K+-induced contraction by 90% was determined and expressed in μM as the effective concentration (EC$_{90}$), given in Table I.

TABLE I

| Compound | Activity Test A EC$_{90}$ μM |
|---|---|
| AA | 0.003 |
| AB | 0.3 |
| BD | 0.00003 |
| BE | 0.003 |

The compounds of general formula (I) and their intermediates can be prepared by the application or adaptation of known methods, for example as hereinafter identified.

By the term "known methods" as used in this specification is meant methods heretofore used or described in the literature, for example in the specifications of European Patent Application Nos. 321,274A and 321,273A and their United States equivalents U.S. Ser. No. 07/285,219 and 07/285,114. The above specifications are hereby incorporated by reference.

According to a feature of the present invention, the compounds of general formula (I) wherein $R^2$ represents the hydrogen atom may be prepared by the reduction of a compound of general formula (III) wherein $R^1$ is a hereinbefore defined for $R^1$ or when n is 1, $R^{1'}$ may represent hydrogen.

The reduction is effected using a reducing agent, e.g. lithium aluminum hydride, sodium borohydride, sodium cyanoborohydride or borane, in an inert organic solvent optionally under inert atmosphere, at 0°–50° C.

According to a feature of the present invention, the compounds of general formula (I) wherein one or both of $R^1$ and $R^2$ represents an optionally substituted alkyl, cycloalkyl, cycloalkylalkyl, aryl, aralkyl, aryloxyalkyl, aromatic heterocyclylalkyl or aromatic heterocyclyloxyalkyl group may be prepared by the reaction of a compound of general formula (I) wherein at least one of $R^1$ and $R^2$ represents the hydrogen atom with the corresponding alkyl, cycloalkyl, cycloalkylalkyl, aryl, aralkyl, aryloxyalkyl, aromatic heterocyclylalkyl or aromatic heterocyclyloxyalkyl halide in the absence or presence of an inert organic solvent, for example an aromatic hydrocarbon, e.g. benzene or toluene, chloroform, dichloromethane, tetrahydrofuran or dimethylformamide, at a temperature of from 0° C. up to the reflux temperature of the reaction mixture.

According to a feature of the present invention, the compounds of general formula (I) wherein one or both of $R^1$ and $R^2$ represents a group ZC(=O)— as hereinbefore defined may be prepared by the reaction of a compound of general formula (I) wherein at least one of $R^1$ and R² represents a hydrogen atom with an acid halide of a compound of general formula

ZCOOH (IV)

or a reactive acid anhydride thereof.

The reaction is effected, optionally in the presence of an acid acceptor, for example a tertiary amine, e.g. triethylamine, or an inorganic base, e.g. sodium bicarbonate, preferably in the presence of an anhydrous inert organic solvent, e.g. chloroform or acetone, and preferably at a temperature of from −30° C. to +30° C.

According to a feature of the present invention, the compounds of general formula (I) wherein R¹ represent a group $ZSO_2$— as hereinbefore defined may be prepared by the reaction of a compound of general formula (I) wherein n is 0 and R¹ represents a hydrogen atom with a sulphonyl halide of the general formula:

ZSO₂X' (V)

wherein Z is as hereinbefore defined and X¹ represents a halogen atom, preferably chlorine.

The reaction is optionally effected in the presence of an acid acceptor, for example a tertiary amine, e.g. pyridine, and preferably at a temperature of from −30° C. to +30° C., preferably at or near 0° C.

The thioformamide derivatives of general formula (I) obtained by the aforedescribed processes can be purified by the usual physical methods, in particular crystallization and chromatography, especially to resolve mixtures of enantiomers using a chiral column.

By the term "pharmaceutically acceptable salts" as used in this specification is meant salts the anions or cations of which are relatively innocuous to the animal organism when used in therapeutic doses so that the beneficial pharmaceutical properties of the parent compounds of general formula (I) capable of forming salts are not vitiated by side effects ascribable to those anions or cations.

As well as being useful in themselves as active compounds, acid addition salts of the compounds of general formula (I) capable of forming such salts are useful for the purposes of purification of the parent compounds of general formula (I), for example exploitation of the solubility differences between the salts and the parent compounds, by techniques well known to those skilled in the art. The parent compounds of general formula (I) can be regenerated from their acid addition salts by known methods, for example by treatment with an alkali, e.g. aqueous sodium bicarbonate solution or aqueous ammonia solution.

Suitable acid addition salts for use in pharmaceuticals may be selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and di-p-toluoyltartrates.

As well as being useful in themselves as active compounds, salts of the compounds of general formula (I) capable of forming salts with bases are useful for the purposes of purification of the parent compounds of general formula (I), for example by exploitation of the solubility differences between the salts and the parent compounds, by techniques well known to those skilled in the art.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts.

In this specification reference to compounds of formula (I) is intended to include reference to their pharmaceutically acceptable salts, where the context so permits.

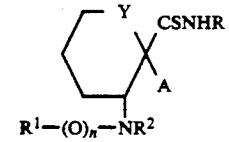

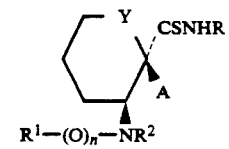

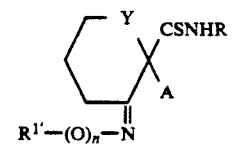

EXAMPLES

The following Examples illustrate the preparation of compounds according to the present invention.

Unless stated otherwise, all the nuclear magnetic resonance (NMR) spectra were recorded at 200 MHz in deuterochloroform; the chemical shifts are expressed in ppm relative to the tetramethylsilane signal. The abbreviations used in the following text are as follows: s=singlet, d=doublet, t=triplet, q=quartet, m=multiplet, c=unresolved bands, and b=broad.

EXAMPLE 1

Compound AA

A stirred solution of (±)-2-benzyloxyimino-N-methyl-1-(3-pyridyl)cyclohexanecarbothioamide (2.5 g) in dry tetrahydrofuran (50 ml) under argon was treated portionwise with lithium aluminum hydride (0.305 g) at 25° and stirred at that temperature for 3.5 hours. The green suspension was cooled in ice and treated dropwise with water (75 ml) at 5°. The mixture was extracted with chloroform (3×75 ml), the combined extracts dried (magnesium sulphate) and evaporated. The residue was subjected to flash chromatography on silica gel eluting with chloroform/methanol: 99/1 followed by washing with hexane to give (±)-trans-2-benzyloxyimino-N-methyl-1-(3pyridyl)cyclohexanecarbothioamide, a colorless solid (1.1 g, 43%), m.p. 136°–137°. Found: C, 67.6; H, 7.02; N, 11.7%; $C_{20}H_{25}N_3OS$ requires C, 67.6; H, 7.09; n, 11.8%.

EXAMPLE 2

Compound AB

Prepared from (±)-2-methoxyamino-N-methyl-1-(3-pyridyl)cyclohexanecarbothioamide (2.5 g) as described in Example 1. The crude product was subjected to flash chromatography on silica gel eluting with chloroform/methanol: 98.5/1.5, washed with hexane to give (±)-trans-2-methoxyamino-N-methyl-1-(3-pyridyl)cyclohexanecarbothioamide, a colorless solid (1.0 g, 40%), m.p. 165°-170°.

EXAMPLE 3

Prepared from (±)-2-(4-fluorobenzyloxyamino)-N-methyl-1-(3-pyridyl)cyclohexanecarbothioamide (4.6 g) as described in Example 1. The crude product was subjected to flash chromatography on silica gel eluting with chloroform/methanol: 98/2, washed with pentane to give (±)-trans-2-(4-fluorobenzyloxyamino)-N-methyl-1-(3-pyridyl) cyclohexanecarbothioamide, a colorless solid (0.9 g, 19%), m.p. 128°-130°. Found: C, 64.6; H, 6.6; N, 11.2%; $C_{20}H_{24}FN_3OS$ requires C, 64.3; H, 6.48; N, 11.0%.

EXAMPLE 4

Compound AD

Prepared from (−)-(S)-2-(2,3,4,5, 6-pentafluorobenzyloxyamino)-N-methyl-1-(3-pyridyl)cyclohexanecarbothioamide (0.49 g) as described in Example 1. The crude product was subjected to flash chromatography on silica gel eluting with chloroform/methanol: 98.5/1.5 to give (1S,2R)-2-(2,3,4,5,6-pentafluoro-benzyloxyamino)-N-methyl-1-(3-pyridyl)cyclohexanecarbothioamide, a yellow solid (0.34 g, 69%), m.p. 57°-60°. Found: C, 53.7; H, 4.37; N, 9.5%; $C_{20}H_{20}F_5N_3OS$ requires C, 53.9; H, 4.53; N, 9.43%.

EXAMPLE 5

Compound AE

A stirred solution of (±)-2-(2-hydroxyethoxyimina-N-methyl-1-(3-pyridyl)cyclohexanecarbothioamide (2.5 g) in dry tetrahydrofuran (45 ml) under argon was treated portionwise with lithium aluminum hydride (0.35 g), the temperature rising to 43°. The mixture was then stirred at 25° for 3 hours. It was then treated with a further quantity of lithium aluminum hydride (0.34 g) and stirred at 25° for 3 hours.

The mixture was cooled in an ice bath and treated dropwise with water (80 ml), extracted with ethyl acetate (3×80 ml), and the combined extracts were dried and evaporated The residue was subjected to flash chromatography on silica gel eluting with chloroform/methanol; 95/5, washed with diethyl ether, to give (±)-trans-2-(2-hydroxyethoxyamino-N-methyl-1-(3-pyridyl)cyclohexanecarbothioamide, a colorless solid (0.43 g, 17%), m.p. 142°-145°. Found: C, 58.0; H, 7.3; N, 13.5. $C_{15}H_{23}N_3O_2S$ requires C, 58.2; H, 7.49; N, 13.6.

EXAMPLE 6

Compound BA

A solution of (±)-2-hydroxyamino-N-methyl-1-(3-pyridyl)cyclohexanecarbothioamide (13.2 g) in dry tetrahydrofuran (500 ml) was added dropwise to a stirred suspension of lithium aluminum hydride (7.66 g) in tetrahydrofuran (250 ml) under argon during 30 minutes. The mixture was heated at reflux for 1.5 hours, and then it was cooled to 5° and treated dropwise with water (750 ml). The mixture was extracted with chloroform (7×350 ml). The combined extracts were dried (magnesium sulphate) and evaporated. The residue was subjected to flash chromatography on silica gel, eluting with ethyl acetate methanol/triethylamine: 90/18/5, washed with diethyl ether, to give (±)-trans-2-amino-N-methyl-1-(3-pyridyl)cyclohexanecarbothioamide, a colorless solid (2.3 g, 19%), m.p. 184°-188°.

EXAMPLE 7

Compound BB

A solution of (±)-trans-2-amino-N-methyl-1-(3-pyridyl)cyclohexanecarbothioamide (0.51 g) in dry pyridine (5.3 ml) was cooled to 0° and treated dropwise with benzoyl chloride (0.29 g) during 16 minutes. Stirring was continued at 0° for 2.5 hours.

The solution was concentrated in vacuo (40°/0.3 mm Hg) and the residue partitioned between chloroform (10 ml) and 2M aqueous sodium carbonate solution. The chloroform layer was washed with water (10 ml), dried (magnesium sulphate) and evaporated. The residue was subjected to flash chromatography on silica gel, eluting with chloroform/methanol: 95/5, washed with diethyl ether to give (±)-trans-2-benzamido-N-methyl-1-(3-pyridyl)cyclohexanecarbothioamide, a yellow solid (0.15 g, 29%), m.p, 125°-130°.

EXAMPLE 8

Compound BC

Prepared from (±)-trans-2-amino-N-methyl-1-(3-pyridyl)cyclohexanecarbothioamide (1.0 g) and acetyl chloride (0.32 g) as described in Example 2. The crude product was subjected to flash chromatography on silica gel eluting with methylene chloride/methanol; 92/8, washed with diethyl ether to give (±)-trans-2-acetamido-N-methyl-1-(3-pyridyl) cyclohexanecarbothioamide, a colorless solid (0.28 g, 24%), m.p. 226°-229°.

EXAMPLE 9

Compounds BD, BE, BF and BG

A mixture of 2-(3-pyridyl)cyclohexanone (10 g, 57 mmol), (R)-1-phenylethylamine (8.1 ml, 68 mmol) and p-toluenesulphonic acid hydrate (0.11 g, 0.57 mmol) in anhydrous toluene (85 ml) was heated at reflux in a Dean-Stark apparatus for 3 hours under an argon atmosphere.

The cooled solution was concentrated in vacuo at 14 mm and 50° C. and then at 0.1 mm and 40° C. to furnish 2-(3-pyridyl)-1-[(R)-1-phenylethylimino]cyclohexane as a crude red oil (18 g) which was used in the next stage without further purification.

A stirred solution of the crude 2-(3-pyridyl)-1-[(R)-1-phenylethylimino]cyclohexane (18 g) in anhydrous tetrahydrofuran (80 ml) at −78° C. was treated dropwise with n-butyllithium (1.6M in hexane) (39.5 ml, 62.8 mol) over 1 hour.

The resulting deep red solution was stirred at −60° C. for a further 1 hour then cooled to −78° C. A solution of methyl isothiocyanate (5 g, 68.6 mmol) in tetrahydrofuran (8 ml) was added dropwise over a period of 10 minutes to the reaction mixture, which was then allowed to warm to 0° C. over a period of 1 hour. After an extra period of 30 minutes at 0° C. the resulting mixture was poured into a cold solution of ammonium chloride (20% w/w) (100 ml). The organic layer was removed and the aqueous layer extracted with diethyl ether (2×100 ml). The combined organic fractions were washed successively with water (100 ml) and brine (100 ml) then dried over magnesium sulphate. Concentration in vacuo gave crude 2-[(R)-1-phenylethylimino]-S-1-(3-pyridyl)cyclohexane-N-methylcarbothioamide as an orange oil (23 g), which was used in the next stage without further purification.

A solution of crude 2-[(R)-1-phenylethylimino]-S-1-(3-pyridyl)cyclohexane-N-methylcarbothioamide (23 g) in anhydrous methanol (70 ml) at 0° C. under an argon atmosphere was treated with sodium cyanoborohydride (9 g, 143 mmol). Glacial acetic acid (9.8 ml, 170 mmol) was then added dropwise to the mixture over a period of 15 minutes at 0° C. The reaction mixture was then allowed to warm to 20° C. over 1 hour and stirred for a further 30 minutes at 20° C. Aqueous sodium carbonate (1.5M) (115 ml, 173 mmol) was then slowly added to the reaction mixture which was then extracted with chloroform (2×200 ml). The combined organic extracts were washed successively with water (200 ml) and brine (50 ml) then dried over sodium sulphate. Concentration under reduced pressure at 30° C. and 14 mm Hg gave a crude red oil which was recrystallized from ethyl acetate to give (2R,1S)-2-[(R)-1-phenylethylamino]-1-(3)-pyridyl) cyclohexane-N-methylcarbothioamide (6.4 g, 18.1 mmol, 32% overall yield) m.p. 165°–166° C. found: C, 71.3%; H, 7.7%; N, 11.9%; S, 9.1%. $[\alpha]^{25}_D = +61°$ (C=0.47, CHCl$_3$) 'H. N.M.R. 1.05–1.805 (m,7H), 1.35 (d,3H), 2.35 (ddd,1H); 2.7 (dd,1H), 3.2 (d,3H), 3.2 (dd,1H), 3.7 (q,1H), 7.2–7.4 (m, 6H), 8.0 (ddd,1H), 8.5 (dd,1H), 8.9 (d,1H), 9.8 (broad s,1H).

In a similar manner the following were prepared:
* (2R,1S)-2-[(R)-1-(1-naphthyl)ethylamino]-1-(3-pyridyl)cyclohexane-N-methylcarbothioamide (recrystallized from ethyl acetate) (47% overall yield) m.p. 204°–205° C. Found: C, 74.4%; H, 7.4%; N, 10.3%; S, 7.8%. C$_{25}$H$_{29}$N$_3$S requires C, 74.4%; H, 7.3%, N, 10.4%; S, 7.9%. $[\alpha]^{25}_D = -70°$ (C=0.5, CHCl$_3$) 'H N.M.R. 1.1–1.65 (m,6H), 1.4 (d,3H), 1.7 (bs,1H); 1.9 (ddd,1H), 2.4 (ddd,1H), 2.6 (dd,1H), 3.2 (d,3H), 3.5 (dd,1H), 4.6 (q,1H), 7.3 (dd,1H), 7.4–7.6 (m,4H), 7.8 (d,1H), 7.9 (dd,1H), 8.1 (m,2H), 8.5 (dd,1H), 9.0 (d,1H), 9.5 (broad s,1H),
* using (R)-1-(1-naphthyl)ethylamine as initial starting material;
** (2R,1S)-2-[(R)-1-cyclohexylethylamino)-1-(3-pyridyl)cyclohexane-N-methylcarbothioamide (subjected to flash chromatography over silica gel, eluting with a 55:40.5 mixture of chloroform, diethyl ether and ethanol, and then recrystallized from ethyl acetate) (17% overall yield) m.p. 138°–139° C. Found: C, 70.1%; H, 9.5%; N, 11.6%; S, 8.9%. C$_{21}$H$_{33}$N$_3$S requires C, 70.1; H, 9.3; N, 11.7; S, 8.9. $[\alpha]^{25}_D = +30°$ (C=0.43, CHCl$_3$); NMR: 0.98 (d, 3H), 0.98–1.6 (m,9H), 1.6–1.9 (m,8H), 2.0–2.2 (m,2H), 2.6 (c,1H), 3.0 (dd,1H), 3.06 (dd, 1H), 3.1 (d,3H), 7.3 (dd,1H), 7.9 (ddd,1H); 8.3 (dd,1H), 8.9 (d,1H), 10.0 (broad s,1H).
** using (R)-1-cyclohexylethylamine as initial starting material; and
*** (±)-(2R,1S)-1-[(R)-1-(4-fluorophenyl)-ethylamino]-2-(3-pyridyl)cyclohexane-N-methylcarbothioamide (subjected to flash column chromatography over silica gel, eluting with 55:40.5 mixture of chloroform, diethyl ether and ethanol, and then recrystallized from ethyl acetate) (10% overall yield) m.p. 130°–135° C. Found: C, 67.8; H, 7.2; N, 11.3; S, 8.6%. C$_{21}$H$_{26}$FN$_3$S requires C, 67.9; H, 7.1; N, 11.3; S, 8.6%; NMR: 1.0–1.2 (m,1H), 1.2–1.8 (c,9H); 2.35 (m,H), 2.5–2.6 (m,1H), 3.1 (d,3H), 3.2–3.3 (dd, 1H), 3.6 (q,1H), 8.5 (m,1H), 8.9 (m,1H), 9.2–9.3 (broad singlet,1H).
*** using (±)-1-(4-fluorophenyl)ethylamine as initial starting material.

EXAMPLE 10

Compound CA

A stirred solution of (±)-trans-2-amino-N-methyl-1-(-3-pyridyl)cyclohexanecarbothioamide (0.5 g) in dry pyridine (5 ml) was treated with benzenesulphonyl chloride (35 g) dropwise at 0° C. Stirring was continued at 0° C. for 1.5 hours. The solution was evaporated in vacuo and the residue was partitioned between water (10 ml) and chloroform (10 ml). The organic phase was washed with water (10 ml), dried, and evaporated. The resulting red oil was subjected to flash chromatography on silica gel, eluting with a mixture of methylene chloride and methanol (96:4 v/v) to give, after trituration with diethyl ether, (±)-trans-N-methyl-2-phenylsulphonamide-1-(3-pyridyl)cyclohexanecarbothioamide (0.16 g), in the form of a pale orange solid, m.p. 254°–255° C. [NMR (400 MHz): 1.3–2.4 (8H,m), 3.0 (3H,d), 4.7 (1H,m), 5.2 (1H,d), 7.1 (1H,g), 7.5 (2H,t), 7.57 (1H,m), 7.62 (1H,br) 7.7 (2H,m), 7.9 (1H,m), 8.4 (1H,m), 8.5 (1H,d)].

EXAMPLE 11

Compounds CB, CC and CD

A stirred suspension of (±)-N-methyl-2-oxo-1-(3-pyridyl)cyclohexanecarbothioamide (2.5 g) and aniline (3.72 g) in anhydrous dichloroethane (30 ml) under an argon atmosphere was treated dropwise at 25° C. with titanium tetrachloride (0.8 ml). The reaction mixture was stirred at 25° C. until completion of the reaction (as judged by TLC analysis), and then it was poured into a solution of sodium bicarbonate (16.8 g) in water (100 ml) and stirred for 15 minutes. The mixture was filtered through a pad of celite and the aqueous layer was extracted with dichloromethane (3×75 ml). The combined organic solution was washed with aqueous sodium bicarbonate solution (100 ml; 10% w/w), with water (50 ml) and with saturated brine (100 ml), and then it was dried over sodium sulphate and concentrated in vacuo, to give N-methyl-2-phenylimino-1-(3-pyridyl)cyclohexanecarbothioamide in the form of a crude oil.

A stirred solution of this crude N-methyl-2-phenylimino-1-(3-pyridyl)cyclohexanecarbothioamide in dichloromethane (15 ml), cooled at 0° C. under an argon atmosphere, was treated with sodium cyanoborohydride (1.6 g), in one portion. Dry methanol (30 ml) was then added, followed by a dropwise addition of glacial acetic acid (3 ml). The temperature was allowed to rise to 25° C. and then the reaction mixture was poured into saturated aqueous sodium bicarbonate solution (150 ml). The aqueous phase was extracted with dichloromethane (3×100 ml) and the combined organic extracts were washed with saturated aqueous sodium bicarbonate solution (100 ml), with water (50 ml) and then with saturated brine (100 ml), dried over sodium sulphate and concentrated in vacuo, to give a crude oil which was crystallized from a mixture of diethyl ether and ethyl acetate, to give (±)-trans-N-methyl-2-phenylimino-1-(3-pyridyl)cyclohexanecarbothioamide (1.9 g, 5.83), m.p. 195°–196° C. [NMR: 1.42–1.67 (m,4H); 1.80–1.90 (m,1H); 2.11–2.18 (m,1H); 2.31–2.37 (m,1H); 2.62–2.70 (m,1H); 3.00 (d,3H); 3.61 (bd,1H); 4.49 (bs,1H); 6.62 (dd,2H); 6.74 (ddt,1H); 7.13 (dt,2H); 7.23 (dd,1H); 7.90 (dt,1H); 8.42 (bs,1H); 8.46 (dd,1H); 8.75 (d,1H). Elemental analysis: C, 70.40; H, 7.20; N, 12.90; S, 9.70%; Calculated: C, 70.10; H, 7.10; N, 12.90; S, 9.80%.

By proceeding in a similar manner, but replacing the aniline by the appropriate quantities of benzylamine and 3-pyridylmethylamine respectively, there were prepared: (±)-trans-N-methyl-benzylamino-1-(3-pyridyl)- cyclohexanecarbothioamide, m.p. 125°–126° C. (from a mixture of diisopropyl ether and diethyl ether) [NMR: 1.25–1.66 (m,5H); 1.73–1.79 (m,1H); 2.11–2.18 (m,1H); 2.25 (dt,1H); 2.73–2.80 (m,1H); 3.04 (d,3H); 3.33 (dd,1H); 3.75 (dd,2H); 7.24–7.37 (m,6H); 8.05 (dt,1H); 8.48 (dd,1H); 8.91 (d,1H); 9.00 (bs,1H); Calculated: C, 70.70; H, 7.40; N, 12.40; S, 9.50%; Found: C, 70.50; H, 7.50; N, 12.30; S, 9.50%], and (−)-(1R,2S)-N-methyl-2-(3-pyridyl)methylamino-1-(3-pyridyl) cyclohexanecarbothioamide, m.p. 141°–142° C. (from ethyl acetate) [NMR: 1.29–1.63 (m,6H); 1.68–1.75 (m,1H); 2.08–2.14 (m, 1H); 2.42 (dt,1H); 2.53–2.59 (m,1H); 3.06 (d,3H); 3.59 (dd,1H); 3.75 (dd,2H); 7.24–7.29 (m,2H); 7.55 (dt,1H); 8.10 (dd,1H); 8.48–8.52 (m,2H); 8.60 (bs,1H); 8.93 (d,1H); Calculated: C, 67.00; H, 7.10; N, 16.45; S, 9.40%; Found: C, 66.80; H, 7.20; N, 16.30; S, 9.60%; $[\alpha]^{25}_D = -66.9°$ (c=0.538, CHCl$_3$).

REFERENCE EXAMPLE 1

A solution of (±)-N-methyl-2-oxo-1-(3-pyridyl) cyclohexanecarbothioamide (0.5 g, 2 mmol) in pyridine (5 ml) at 60° C. was treated with O-benzylhydroxylamine hydrochloride (0.65 g, 4 mmol) and the resulting mixture was then stirred for 24 hours at 60° C. The reaction mixture was then stirred for 24 hours at 60° C. The reaction mixture was partitioned between water (50 ml) and ethyl acetate (25 ml) and the aqueous layer was then extracted with ethyl acetate (2×25 ml). The combined organic extracts were washed with brine (50 ml) then dried over magnesium sulphate. Concentration in vacuo gave a crude oil which was recrystallized from ethyl acetate to give (±)-anti-N-methyl-2-benzyloxyimino-1-(3-pyridyl) cyclohexanone (0.57 g, 1.6 mmol), m.p/128°–130° C. NMR: 1.48 2.15 (c,4H); 2.16–2.40 (m,2H); 2.8–2.96 (m,2H); 2.96–3.04 (d,3H); 5.02–5.08 (s,2H); 7.12–7.22 (c, 3H), 7.32–7.44 (c,3H); 7.44–7.56 (m,2H); 8.16–8.38 (bs,1H); 8.38–8.52 (c,2H); Found: C, 67.7; H, 6.5; N, 1119; S, 9.0%; Calculated: C, 68.0; H, 6.6; N, 11.9; S, 9.1%.

REFERENCE EXAMPLE 2

By proceeding in a similar manner to that described in Reference Example 1, there was prepared (−)-(S)-anti-2-(2,3,4,5,6-pentafluorobenzyloxyimino)-N-methyl-1-(3-pyridyl) cyclohexanecarbothioamide, m.p. 115°–116° C., from (S)-N-methyl-2-oxo-1-(3-pyridyl)cyclohexanecarbothioamide.

The present invention includes, within its scope, pharmaceutical compositions which contain one or more compounds of general formula (I), or pharmaceutically acceptable salts thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders, and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting and suspending agents, and sweetening, flavoring, perfuming, and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions, and emulsions. Examples of organic solvents or suspending media are propylene glycol, polyethylene glycol, vegetable oils such as olive oil and injectable organic esters such as ethyl oleate. The compositions may also contain adjuvants such as stabilizing, preserving, wetting, emulsifying and dispersing agents. They may be sterilized by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulized or dry powders formulated in accordance with known methods.

Solid compositions for rectal administration include suppositories formulated in accordance with known methods and containing one or more of the compounds of formula (I) or pharmaceutically acceptable salts thereof.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from 0.001 to 50 mg/kg body weight per day by oral administration. By inhalation the preferred daily dosage is from 0.001 to 5 mg/kg body weight.

The compounds may also be applied topically for inhibition of head hair loss associated with male pattern baldness, the preferred daily dosage being from 0.1 to 10 mg/kg body weight applied, for example, in 5 ml portions two or three times per day.

The following Composition Example illustrates pharmaceutical compositions according to the present invention.

COMPOSITION EXAMPLE

No. 2 size gelatin capsules each containing:

| | |
|---|---|
| (±)-trans-2-benzyloxyamino-N-methyl-1-(3-pyridyl) cyclohexane-carbothioamide | 20 mg |
| lactose | 100 mg |
| starch | 60 mg |
| dextrin | 40 mg |
| magnesium stearate | 1 mg | were prepared in accordance with the usual procedure.

Although the invention has been described in conjunction with specific embodiments, it is evident that many alternatives and variations will be apparent to those skilled in the art in light of the foregoing description. Accordingly, the invention is intended to embrace

We claim:

1. A thioformamide compound of the formula

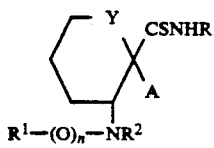

wherein R represents a straight- or branched chain alkyl radical containing 1 to 4 carbon atoms, A represents an aromatic heterocyclic radical selected from the group consisting of pyrid-3-yl and Y represents a valency bond or a methylene or ethylene radical, $R^2$ represents hydrogen, or $R^2$ represents a group ZC(=O)— in which Z represents phenyl, pyrid-3-yl or thien-2-yl group or a straight- or branched-chain alkyl group containing from 1 to 6 carbon atoms, each of which may be optionally substituted by at least one substituent selected from halogen or hydroxy, $C_{1-4}$-alkyl, $C_{2-4}$-alkenyl, $C_{1-4}$-alkoxy, tetrahydropyranyloxy, cyano, nitro, trifluoromethyl, carboxy, benzoylamino, quarternary ammonium, amino, $C_{1-4}$-alkylamino and di-$C_{1-4}$-alkylamino groups, optionally substituted by hydroxy groups, $C_{2-5}$-alkoxy carbonylamino, $C_{2-5}$-alkanoylamino or $C_{2-5}$-alkoxycarbonyl groups or carbamoyl, unsubstituted or substituted by one or two $C_{1-4}$-alkyl groups in turn optionally substituted by hydroxy groups, piperidinocarbonyl, or represents a benzyl, phenethyl, 1-naphthylmethyl, 2-naphthylmethyl, pyridyl-3-ylmethyl, n represents 0 or 1, and when n represents 0, $R^1$ represents hydrogen, an optionally substituted $C_{1-4}$-alkyl, cyclohexyl, pyridyl, benzyl, phenethyl, 1-naphthylmethyl, 2-naphthylmethyl, pyridyl-3-ylmethyl or $C_{6-12}$-aryl, said optional substituents being halogen, hydroxy, $C_{1-4}$-alkyl, $C_{1-4}$-alkoxy, $C_{2-4}$-alkenyl tetrahydropyranyloxy, cyano, nitro, trifluoromethyl, carboxy, benzoylamino, quarternary ammonium, amino, $C_{1-4}$-alkylamino and di-$C_{1-4}$-alkylamino optionally substituted by hydroxy group, $C_{2-5}$-alkoxy carbonylamino, $C_{2-5}$-alkanoylamino or $C_{2-5}$-alkoxycarbonyl or carbamoyl, unsubstituted or substituted by one or two $C_{1-4}$-alkyl groups in turn optionally substituted by hydroxy groups, or piperidinocarbonyl or a group ZC(=O)— or $ZSO_2$, and when n represents 1, $R^1$ represent a straight- or branched-chain alkyl radical containing from 1 to 4 carbon atoms which is unsubstituted or substituted by at least one substituent selected from $C_{2-4}$-alkenyl, carboxy, $C_{2-5}$-alkoxycarbonyl, hydroxy, $C_{1-4}$-alkoxy, carbamoyl, unsubstituted or substituted by one ore two $C_{1-4}$- alkyl groups, amino, $C_{1-4}$-alkylamino and di-$C_{1-4}$-alkylamino groups or represents a benzyl, phenethyl, 1-naphthylmethyl, 2-naphthylmethyl or pyrid-3-ylmethyl radical each of which may be substituted on the ring by at least one halogen atom or hydroxy, $C_{1-4}$-alkyl, $C_{1-4}$-alkoxy, alkoxy being unsubstituted or substituted as defined for alkyl groups represented by $R^1$, cyano, nitro, trifluoromethyl, carboxy, $C_{1-4}$-alkylamino, $C_{2-5}$-alkanoylamino or $C_{2-5}$-alkoxycarbonyl groups, and pharmaceutically acceptable salts thereof.

2. A compound according to claim 1, wherein Y represents methylene.

3. A compound according to claim 1, wherein A represents 3-pyridyl, 6-chloropyrid-3-yl or 5-bromopyrid-3-yl.

4. A pharmaceutical composition which comprises an effective amount of at least one thioformamide compound according to claim 1 or a pharmaceutically acceptable salt thereof in association with a pharmaceutically acceptable carrier or coating.

5. A method for achieving an effect in a patient comprising administering an effective amount of at least one thioformamide compound according to claim 1 to the patient or a pharmaceutically acceptable salt thereof wherein the effect is treatment or prophylaxis of disorder associated with vascular smooth muscle contraction, respiratory smooth muscle contraction, contraction of smooth muscle of gastrointestinal tract, urinary bladder and uterus.

6. A compound according to claim 1, wherein Z represents a phenyl, pyrid-3-yl or thien-2-yl group or a straight- or branched-chain alkyl group (containing from 1 to 6 carbon atoms), each of which may be optionally substituted by one or more substituents selected from halogen atoms or hydroxy, $C_{1-4}$-alkyl, $C_{2-4}$-alkenyl, $C_{1-4}$-alkoxy, tetrahydropyranyloxy, cyano, nitro, trifluoromethyl, carboxy, benzoylamino, quaternary ammonium, amino, $C_{1-4}$-alkylamino and di-$C_{1-4}$-alkylamino groups (optionally substituted by hydroxy groups), $C_{2-5}$-alkoxy carbonylamino, $C_{2-5}$-alkanoylamino or $C_{2-5}$-alkoxycarbonyl groups or carbamoyl (unsubstituted or substituted by one or two $C_{1-4}$-alkyl groups in turn optionally substituted by hydroxy groups) and two substituents on the nitrogen atom may together form a straight or branched chain divalent radical containing from 4 to 6 atoms in the chain which may contain a further heteroatom option, or Z represents a benzyl, phenethyl, 1-naphthylmethyl, 2-naphthylmethyl or pyrid-3-ylmethyl radical.

7. A compound according to claim 1, wherein Z represents a phenyl, 4-fluorophenyl, 3,4-difluorophenyl, 4-methoxyphenyl, 2-carboxyphenyl, pyrid-3-yl, thien-2-yl, methyl, butyl, 2-carboxyethyl, 2-methoxycarbonylethyl, hydroxymethyl, tetrahydropyranyloxymethyl, aminomethyl, t-butoxycarbonylaminomethyl, benzylaminomethyl, benzyl, phenethyl or N-methylpiperidinocarbonylethyl group.

8. A compound according to claim 1, wherein $R^2$ represents a hydrogen atom.

9. A compound according to claim 1, wherein the amino group $R^1R^2N$— is 1-phenylethylamino, 1-(1-naphthyl)ethylamino, 1-cyclohexylethylamino or 1-(pyrid-3-yl)ethylamino.

10. A compound according to claim 1, which comprises one or more of the following features:
   (i) R represents methyl;
   (ii) A represents 3-pyridyl;
   (iii) Y represents methylene;
   (iv) Z represents lower alkyl or optionally substituted phenyl;
   (v) $R^2$ represents hydrogen;
   (vi) $R^1$ represents hydrogen, lower alkyl, optionally carrying a substituent selected from naphthyl and optionally substituted phenyl or 3-pyridyl, cycloalkyl and hydroxy groups, or represents a lower alkanoyl or aroyl or arylsulphonyl group.

11. A compound according to claim 1, which is (±)-trans-2-benzyloxyamino-N-methyl-1-(3-pyridyl)-cyclohexanecarbothioamide (±)-trans-2-methoxyamino-N-methyl-1-(3-pyridyl)cyclohexanecarbothioamide (±)-trans-2-(4-fluorobenzyloxyamino)-N-methyl-1-(3-pyridyl)cyclohexanecarbothioamide (1S,2R)-2-(2,3,4,5, 6-pentafluorobenzyloxyamino)-N-methyl-1-(3-pyridyl)cyclohexanecarbothioamide (±)-trans-2-(2-hydroxyethoxyamino-N-methyl-1-(3-pyridyl)cyclohexanecarbothioamide (±)-trans-2-amino-N-methyl-1-(3-pyridyl)cyclohexanecarbothioamide (±)-trans-2-benzamido-N-methyl-1-(3-pyridyl)cyclohexanecarbothioamide (±)-trans-2-acetamido-N-methyl-1-(3-pyridyl)cyclohexanecarbothioamide (2R,1S)-2-((R)-1-phenylethylamino)-1-(3-pyridyl)cyclohexane-N-methylcarbothioamide (2R,1S)-2-((R)-1-(1-naphthyl)ethylamino)-1-(3-pyridyl)cyclohexane-N-methylcarbothioamide (2R,1S)-2-((R)-1-cyclohexylethylamino)-1-(3-pyridyl)cyclohexane-N-methylcarbothioamide (±)-(2R,1S)-2-((R)-1-(4-fluorophenyl)-ethylamino)-1-(3-pyridyl)cyclohexane-N-methylcarbothioamide (±)-trans-N-methyl-2-phenylsulphonamido-1-(3-pyridyl)-cyclohexanecarbothioamide (±)-trans-N-methyl-2-phenylamino-1-(3-pyridyl)cyclohexanecarbothioamide (±)-trans-N-methyl-1-benzylamino-2-(3-pyridyl)cyclohexanecarbothioamide (−)-(1R,2S)-N-methyl-2-(3-pyridyl)methylamino-1-(3-pyridyl)-cyclohexanecarbothioamide.

* * * * *